(12) United States Patent
Farley

(10) Patent No.: US 7,097,864 B2
(45) Date of Patent: Aug. 29, 2006

(54) PAIN MANAGEMENT COMPOSITION COMPRISING PLANT EXTRACTS

(76) Inventor: Michael D. Farley, 225 Fifth Ave. Suite #6, Indialantic, FL (US) 32903

( * ) Notice: Subject to any disclaimer, the term of this patent is extended or adjusted under 35 U.S.C. 154(b) by 0 days.

(21) Appl. No.: 10/744,126

(22) Filed: Dec. 24, 2003

(65) Prior Publication Data

US 2005/0142177 A1    Jun. 30, 2005

(51) Int. Cl.
*A61K 36/481*    (2006.01)
*A61K 36/82*    (2006.01)
*A61K 36/00*    (2006.01)

(52) U.S. Cl. ...................... 424/725; 424/729; 424/741
(58) Field of Classification Search ................ 424/725, 424/729, 741
See application file for complete search history.

*Primary Examiner*—Patricia Leith
(74) *Attorney, Agent, or Firm*—Bidyut K. Niyogi

(57) ABSTRACT

The present invention relates to a transdermal pain composition consisting of astragalus extract, cat's claw extract, mistletoe extract, sheep sorrel extract, green tea extract, capsaicin, nettle leaf extract, skull cap extract, l-glutamine and fat soluble ascorbyl palmitate in the form of vitamin c.

6 Claims, No Drawings

PAIN MANAGEMENT COMPOSITION COMPRISING PLANT EXTRACTS

BACKGROUND OF THE INVENTION

This invention relates to the control and regulation of pain management. It is common knowledge that all human beings at sometime in their lifetime are afflicted with pain. Consequently, numerous forms of remedies have been proposed and suggested for external body surface use.

BRIEF SUMMARY OF THE INVENTION

The present invention is a transdermal pain formulation. In particular, this inventive formula is designed, for convenience, to be used as a roll on for topical application, in and around the areas of pain.

It should be noted that this formulation could also be in viscous or liquid form, for application as a cream or liquid or spray.

This inventive transdermal formulation assists to block both inflammatory processes and transmission of paint signals simultaneously. It is also designed to facilitate wound healing and trauma recovery.

These mechanisms include, but are not limited to and may find other applications.
1. Prostaglandin inhibition to reduce inflammation
2. Inhibition of substance P to inhibit pain signal transmission
3. Antioxidant properties
4. Scavenging Hydroxyl Free Radicals
5. Scavenging Superoxide Free Radicals
6. Enhances the ability of Phagocytes
7. Enhances the ability of Macrophages to function as Phagocytes
8. Helps control the release of inflammatory mediators such as eicosanoids and hydrolytic enzymes secreted by macrophages
9. Controls levels of Interleukin 1 and Tumor Necrosis Factor
10. Inhibits the genetic transcription factor that activates TNF-a and IL-1B in synovial tissue
11. Stimulation if the proliferation of Fibroblasts
12. Stimulates the production of Fibroplasia (Connective Tissue produces within the body as part of the healing process for Wounds)
13. Inhibition of COX-1
14. Inhibition of COX-2
15. Inhibition of 5-LO
16. Inhibition of LTC-4

According to the present invention, a transdermal pain formulation composition consists of the following substances
a. astragalus at 5% to 16% of the total composition,
b. cat's claw at 6% to 15% of the composition,
c. mistletoe at 5% to 16% of the composition,
d. sheep sorrel at 5% to 15% of the composition,
e. green tea at 6% to 16% of the composition,
f. capsaicin at 5% to 15% of the composition,
g. nettle leaf at 5% to 16% of the composition,
h. skullcap at 6% to 15% of the composition,
i. L-glutamine at 6% to 15% of the composition,
j. fat soluble ascorbyl palmitate form of vitamin C 5% to 15% of the composition, and
k. a transdermal liposomal carrier in which substances (a) to (j) are mixed with alcohol-$H_2O$ tincture to constitute active substances and subsequently to mix with (k) to form a composition mix of the about 40% to 65% of the carrier and about 30 to 50% of the active substances.

The substances in (a) to (j) constitute the active substances of the total mix. The invention also includes a process for pain formulation having a composition consisting of the following substances including
a. astragalus at about 10% of the composition,
b. cat's claw at about 10% of the composition,
c. mistletoe at about 10% of the composition,
d. sheep sorrel at about 10% of the composition,
e. green tea at about 10% of the composition,
f. capsaicin at about 10% of the composition,
g. nettle leaf at about 10% of the composition,
h. skull cap at about 10% of the composition,
i. l-glutamine at about 10% of the composition,
j. fat soluble ascorbyl palmitate form of Vitamin C at about 10% of the composition, and
k. a transdermal liposomal carrier adapted to act as a transdermal carrier in which the substances (a) to (j) are mixed with alcohol $H_2O$ tincture, with a ratio of 1 to 1 to 1 on all herbal components and concentrated to about 50% reduction, to a final addition of ascorbyl palmitate and chondroitin sulfate A (CSA-A) in a ½ (half) to ½ (half) ratio of the concentration about 50% reduction, so that the transdermal carrier at about 60% with about 40% of the total mix of all substances is constituted to form a roll-on application device.

BRIEF DESCRIPTION OF THE INVENTION

The present invention will now be described, by way of example only as follows: This formula is designed to be used as a roll on for topical application. This inventive transdermal formulation assists to block both inflammatory processes and transmission of pain signals simultaneously.

Advantageously the present invention includes an addition of ascorbyl palmitate and l-glutamine in a half to half ratio to the active substances.

Conveniently, the invention also includes a further step by the added substances, when mixed with alcohol-$H_2O$ tincture and condensed and concentrated to a volume of about 50% of the original mix.

Suitably, this invention provides additional features for use as a roll-on the composition is characterized by about 40% active substances and carried in the transdermal liposomal carrier, which constitutes about 60% of the total mix.

In further form, the invention also includes each substance in (a) to (j) in the total composition with an individual content of about 9% to about 11%.

More, specifically each substance (a) to (j) in the total composition has an individual content of about 10% per substance.

It is extremely advantageous to formulate a composition in which the transdermal carrier constitutes about 60% of the final mix with about 40% of the active concentrated combined substances, so as to provide the total transdermal composition as a roll-on.

Suitably, the process provides a specific ratio of the transdermal carrier that is about 60% of the total substance mix to which is added about 40% of active substances to constitute a roll-on device for external surface use on the body.

What I claim is:
1. A transdermal pain formula composition consisting of the following substances:
(a) astragalus alcohol/water extract at 5% to 16% of the total composition,

(b) cat's claw alcohol/water extract at 6% to 15% of the total composition,
(c) mistletoe alcohol/water extract at 5% to 16% of the composition,
(d) sheep sorrel alcohol/water extract at 5% to 15% of the composition,
(e) green tea alcohol/water extract at 6% to 16% of the composition,
(f) capsaicin at 5% to 15% of the composition,
(g) nettle leaf alcohol/water extract at 5% to 16% of the composition,
(h) skullcap alcohol/water extract at 6% to 15% of the composition,
(i) l-glutamine at 6% to 15% of the composition,
(j) fat soluble ascorbyl palmitate in the form of vitamin C at 5% to 15% of the composition, and
(k) a transdermal liposomal carrier.

2. The composition of claim 1 wherein said composition is made up of 40% to 65% of (k) and about 50% of the substances (a)–(j).

3. The composition of claim 1 wherein said composition is made up of 40% of the substances (a)–(j) and 60% transdermal carrier, wherein said composition is carried in the transdermal carrier and wherein said composition is used as a roll-on.

4. The composition of claim 1 wherein said composition is made up of about 40% of the substances (a)–(j) and about 60% of (k) and wherein said composition is used as a roll-on.

5. The composition of claim 1 wherein each substance (a) to (j) is present at a ratio of 1:1:1:1:1:1:1:1:1:1.

6. A transdermal pain formula composition consisting of the following substances:
(a) astragalus alcohol/water extract at about 10% of the total composition,
(b) cat's claw alcohol/water extract at about 10% of the total composition,
(c) mistletoe alcohol/water extract at about 10% of the composition,
(d) sheep sorrel alcohol/water extract at about 10% of the composition,
(e) green tea alcohol/water extract at about 10% of the composition,
(f) capsaicin at about 10% of the composition,
(g) nettle leaf alcohol/water extract at about 10% of the composition,
(h) skullcap alcohol/water extract at about 10% of the composition,
(i) l-glutamine at about 10% of the composition,
(j) fat soluble ascorbyl palmitate in the form of vitamin C at about 10% the composition, and
(k) a transdermal liposomal carrier, wherein said composition is used as a roll-on.

* * * * *